United States Patent [19]

Jordan

[11] Patent Number: 5,005,721
[45] Date of Patent: Apr. 9, 1991

[54] VIAL SEAL

[75] Inventor: Willie W. Jordan, Garland, Tex.

[73] Assignee: Abbott Laboratories, Abbott Park, Ill.

[21] Appl. No.: 177,816

[22] Filed: Apr. 7, 1988

Related U.S. Application Data

[63] Continuation-in-part of Ser. No. 47,831, May 8, 1987, abandoned.

[51] Int. Cl.$^5$ .............................................. A47G 19/00
[52] U.S. Cl. ................................. 220/23.4; 220/23.83; 220/307; 220/339; 220/DIG. 19; 422/102
[58] Field of Search ............... 206/197, 427; 220/23.4, 220/23.8, 23.83, 23.2, 379, DIG. 19, 307, 339; 150/55; 211/74, 76, 84; 422/102, 104

[56] References Cited

U.S. PATENT DOCUMENTS

| | | | |
|---|---|---|---|
| 2,655,282 | 10/1953 | Dunbar | 220/21 |
| 2,949,204 | 8/1960 | Edwards | 220/23.4 |
| 2,992,501 | 7/1961 | Douglas | 220/23.8 |
| 3,021,001 | 2/1962 | Donofrio | 220/23.4 |
| 3,139,208 | 6/1964 | Irwin et al. | 220/23.8 |
| 3,521,785 | 7/1970 | Bergmann et al. | 422/104 |
| 3,601,253 | 8/1971 | Poupitch | 206/197 |
| 3,923,155 | 12/1975 | Tanzer | 206/427 |
| 4,291,803 | 9/1981 | Perales | 206/443 |
| 4,310,488 | 1/1982 | Rahm et al. | 220/23.4 |
| 4,338,383 | 7/1982 | Jutte et al. | |
| 4,348,207 | 9/1982 | Cappel | 422/102 |
| 4,551,308 | 11/1985 | Mintz | 215/6 |
| 4,599,314 | 7/1986 | Shami | 220/23.4 |

FOREIGN PATENT DOCUMENTS

| | | | |
|---|---|---|---|
| 1565458 | 1/1968 | France | 220/23.4 |
| 2431190 | 8/1980 | France | |

Primary Examiner—David T. Fidei
Attorney, Agent, or Firm—Roberta L. Hastreiter; Thomas M. Breininger

[57] ABSTRACT

A vial seal is provided for sealing a plurality of reagent-containing vials seated in a reagent pack. The vial seal comprises a pliable cover having attached thereto a plurality of vial inserts for sealing a corresponding plurality of such vials. The pliable cover contains a corresponding plurality of openings which fit around the necks of the vials to allow the vial seal to remain with the vials at all times. The pliable cover contains a fastener which allows the vial seal to be held in a non-interfering position with respect to the vial openings when the inserts are disengaged from the vials.

1 Claim, 3 Drawing Sheets

VIAL SEAL

This application is a continuation-in-part of Application Ser. No. 07/047,831 filed May 8, 1987 entitled "Vial Seal" by Willie W. Jordan now abandoned.

FIELD OF THE INVENTION

This invention relates to seals for closing containers. More specifically, this invention relates to a seal for enclosing a group of reagent-containing vials arranged in a reagent pack for use with automated clinical analyzer apparatus.

BACKGROUND OF THE INVENTION

In the field of diagnostic testing of biological fluids for the presence of drugs, viral disease, bacterial infections, and the like, samples are collected, reacted with reagents, and the results of the reactions analyzed using well-known techniques. The reagents used in such tests are typically purchased in and drawn from vials or other containers which are often arranged for convenience in pre-formed packs having a plurality of such vials containing the reagents required for a specific test. For economy and practicality, each vial typically contains an aliquot of reagent sufficient to test a number of samples. Such a reagent pack is described in the co-pending application Ser. No. 047,737 entitled Reagent Pack and Carousel filed in the name of Walter Jordan on May 8, 1987, and commonly assigned herewith.

A problem with such "multiple dose" reagent packs is that once opened, the reagents may become contaminated. For example, the properties of certain reagents may be affected by exposure to light or air, the passage of time or exposure to other reagents or contaminants.

The vials of such packs could be individually reclosed using individual screw on or other closures typically provided with such vials. However, such individual closures can be misplaced or lost when separated from their vials. In addition, it is time consuming and inconvenient to individually open and reclose each vial of a pack with a separate closure, particularly in an automatic testing environment where test set-up time and the time between tests can have a critical impact on throughput.

Thus, a need exists for a vial seal apparatus that provides expedient, economical and safe re-sealing of multiple dose reagent vials, once opened. A desirable feature of such an apparatus is to provide re-sealing of a group of vials arranged in a reagent pack. Another desirable feature is to provide an apparatus which minimizes contamination during handling and loss of the seal during the useful life of the reagents. It is advantageous to provide an apparatus that remains attached to, without interfering with, the vials of a reagent pack during use of the reagent pack in an automated clinical analyzer.

SUMMARY OF THE INVENTION

This invention, therefore, seeks to provide a vial seal which provides economical and expedient sealing of the vials contained in a reagent pack. The vial seal of the invention is adapted to be attached removably to the vials throughout storage, as well as when the reagent pack is in use. In addition, the vial seal of the present invention, once attached, forms a single unit with its associated reagent pack.

The vial seal of the present invention, therefore, comprises a number of vial inserts which are attached to a thin, pliable connecting cover in a linear arrangement corresponding to the openings of a number of reagent-containing vials in a reagent pack. The cover is capable of being so that each insert can be individually inserted into or removed from the opening of its corresponding vial. The cover has a series of linearly-arranged openings which are adapted to fit over and around the necks of the reagent-containing vials so that the vial seal is removably attached to the necks of the reagent-containing vials. In the preferred embodiment, the cover includes a first portion and a second portion. The first portion has first and second surfaces with the vial inserts formed on and projecting away from the first surface. The first surface is also flared in a direction from an inner end to a free outer end.

In addition, the vial seal of the present invention includes a post with a ball-shaped end and a corresponding aperture, both formed in the pliable cover. In the preferred embodiment the aperture is located in a midsection of the cover between the first and second portions. When the reagent pack is being used, the ball-shaped end is adapted to be fitted into the aperture to position the inserts away from the openings of the vials to prevent interference with the operation of a clinical analyzer or other instrument. The openings remain over and around the necks of the vials so that the vial seal remains with the reagent pack even during testing.

BRIEF DESCRIPTION OF THE DRAWINGS

The features which characterize the invention are set forth in the appended claims. The invention itself, together with further features and attendant advantages, will be best understood by reference to the following detailed description of a presently preferred embodiment thereof, taken in conjunction with the accompanying drawings, in which:

DETAILED DESCRIPTION OF A PRESENTLY PREFERRED EMBODIMENT

Figure 1:
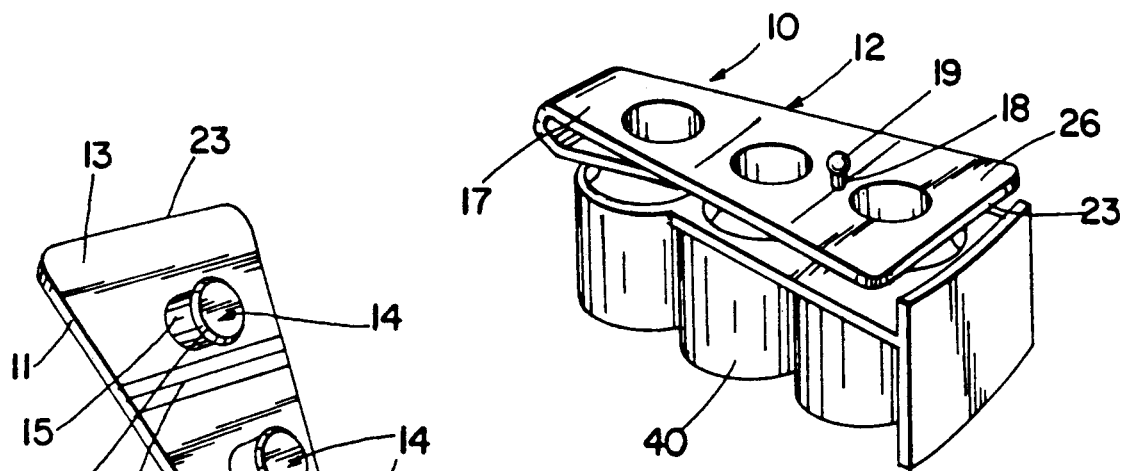
FIG. 1 is a perspective view of the vial seal of the present invention attached to and in sealing contact with vials in a reagent pack.
Figure 2:
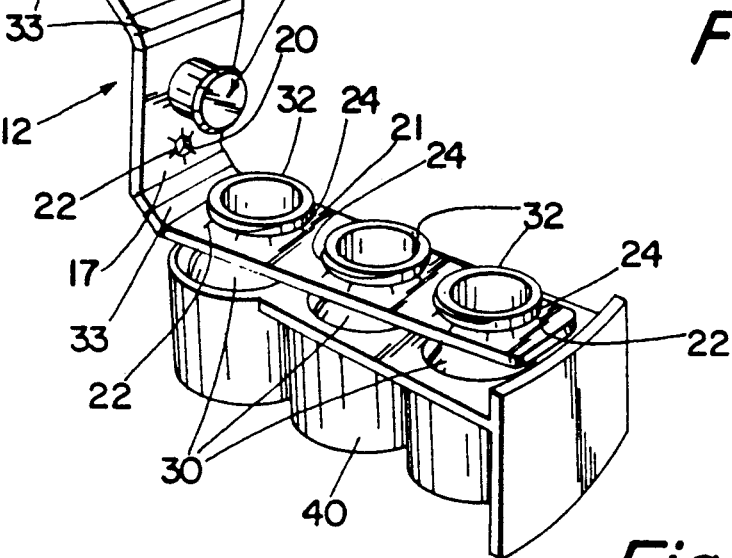
FIG. 2 is a perspective view of the vial seal of the present invention illustrating the vial inserts thereof and the openings thereof placed over and around the necks of the vials in the reagent pack.
Figure 3:
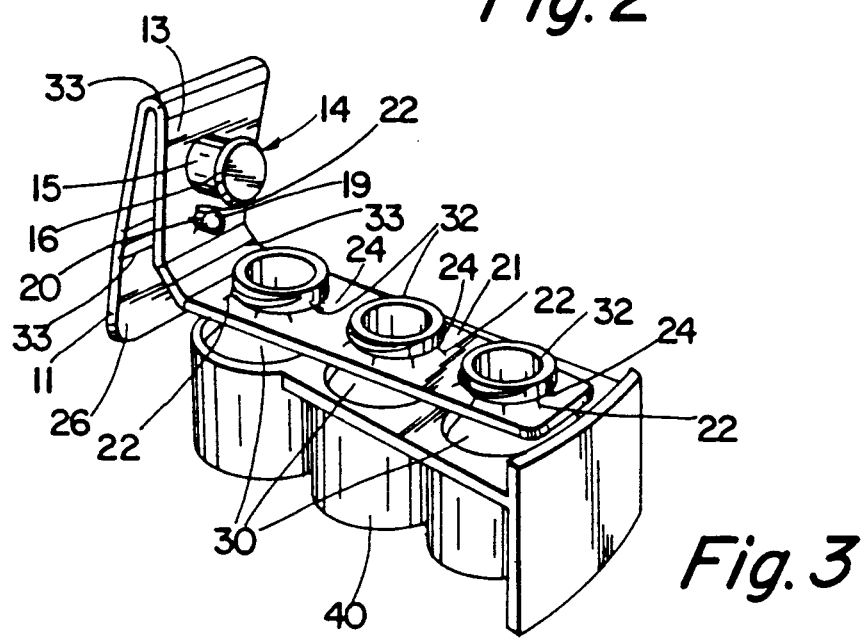
FIG. 3 is a perspective view of the vial seal of the present invention illustrating the ball-shaped end placed through the hole in the pliable cover to hold the inserts in a non-interfering position.

As seen in FIGS. 1, 2 and 3, one embodiment of the present invention comprises a vial seal 10 having a pliable cover 12. One surface of the connecting cover 12 has formed thereon a series of vial inserts 14. Each insert 14 has a cylindrical base 15 and a rib 16 located near the end of the insert 14. Each of the inserts 14 corresponds to an opening of a vial 30 which is mounted in a reagent pack 40. More specifically, cover 12 has a first portion 11 having first 13 and second 26 surfaces and a second portion 21. Vial inserts 14 are positioned on the first surface 13 of the first portion 11 which also has an inner end 17 and outer end 23. In the preferred embodiment, the first portion 11 is flared from the inner end 17 toward the outer end 23. This "wing-type" configuration of the first portion 11 provides a finger grip surface proximate the outer end 23. This finger grip area provides for opening and closing the cover 12 without touching the sealing portions 14 of cover 12, thereby minimizing cross-contamination of the reagents. Each of the inserts 14, like the connecting cover 12, is formed of a pliable plastic. When an insert 14 is inserted into the opening of a vial 30 formed by a neck 32, the insert 14 flexibly forms to and provides a secure fluid-tight press fit in the opening of the vial 30. Referring to FIG. 3, a tight press fit of insert 14 into vial 30 is enhanced by an optional enlarged portion or rib 16 of insert 14. The fluid-tight seal provided by the insert 14 prevents contamination of the reagent by other reagents, samples, or the environment.

In the preferred embodiment, the inserts 14 are arranged linearly along the first surface 13 of the first portion 11 to accommodate a linear arrangement of vials 30 when mounted in the reagent pack 40. Other geometries may also be used to accommodate various reagent pack configurations. The inserts 14 are formed along the first surface 13 of the pliable cover 12 at spacings corresponding to the spacings of the necks 32 of each of the vials 30. Ribs or joints 33 are preferably formed in the cover 12 intermediate each of the inserts 14 to further facilitate bending of the cover 12.

In addition to the inserts 14, the pliable cover 12 also contains a series of openings 24, each corresponding to one of the vials 30 in the reagent pack 40. As best seen in FIG. 2, the openings 24 are aligned along the second portion 21. Each of the openings 24 preferably has a plurality of scores 22 extending radially therefrom and cut into the cover 12. The radiating scores 22 provide flexibility to allow the openings to be fitted over and around the necks of their respective vials, including any flanges or threaded portions formed thereon. The scores 22 also allow the openings 24, once in place, to grip the necks 32 of the vials 30 and remain firmly in place. The openings 24 on the second portion 21 of the vial seal 10 remain attached to the necks 32 of the vials 30 even when the inserts 14 on the first surface 13 of the first portion 11 are disengaged from the openings in the vials 30. Thus, the vial seal 10, once mounted on the vials 30 of a reagent pack 40, remains attached as a single unit with the reagent pack 40 until the vials 30 are emptied. While in the embodiment of FIGS. 1–3 the vial seal 10 is intended to be disposable when vials 30 are empty, the vial seal 10 is removable and could be used with another reagent pack.

The vial seal 10 also contains on the surface 26 opposite the inserts 14 means for securely positioning the inserts 14 proximate the vials 30 when the inserts 14 are disengaged from the vials. In its preferred embodiment the positioning means comprises a cooperating shaft and receiving aperture which the shaft securably engages. Most preferably, as shown in FIG. 3 the shaft is a post 18 with a generally ball-shaped end 19. The post 18 and ball-shaped end 19 correspond to the aperture 20 located between the last of the inserts 14 on the first portion 11 and the first of the openings 24 on the second portion 21, as seen in FIG. 2. The cover 12 can be "folded" as seen in FIG. 3, in such a way that the ball-shaped end 19 aligns with and fits through the aperture 20. When the end 19 is inserted into the aperture 20, the vial seal is maintained in a position wherein the inserts 14 are held in proximity to the vials 30 of the reagent pack 40, but are removed from the space above the necks 32 of the vials 30 so as not to interfere with access to the reagents contained therein by a clinical analyzer, for example. This feature allows the vial seal 10 to remain as a single unit with a set of reagent vials 30 in a reagent pack 40 at all times.

The aperture 20 preferably contains radiating scores 22 similar to those associated with the openings 24. The scores 22 facilitate insertion of the ball-shaped end 19 of the post 18 through the aperture 20. Once the ball-shaped end 19 of the post 18 is inserted through the aperture 20, the radiating scores 22 help keep the ball-shaped end 19 in place.

It should be noted that although a particular configuration of the vial seal 10 which is adapted for use with a particular reagent pack 40 has been described and illustrated, the vial seal 10 is advantageously used with reagent packs having different configurations as well. For example, although the reagent pack 40 as shown in the figures contains three vials 30, alternate embodiments such as the four vial configuration of the referenced application, as well as other configurations, are entirely conducive to the use of similar alternate embodiments of the present vial seal 10.

Figure 4:
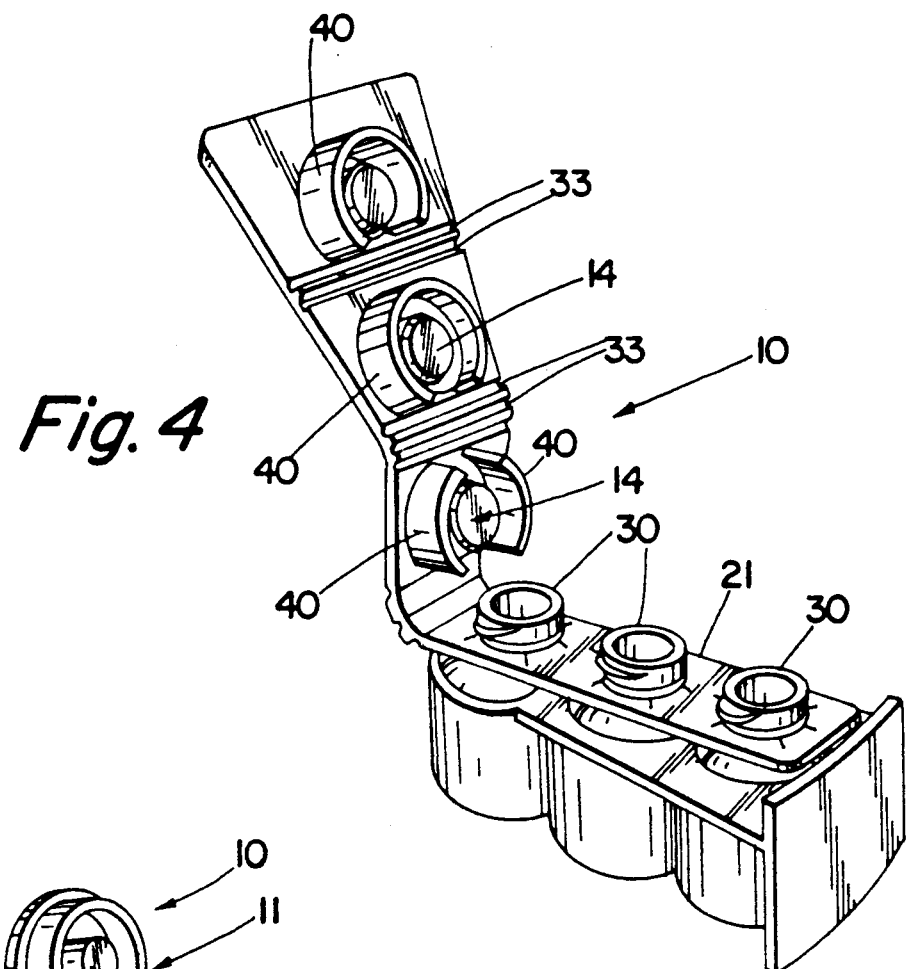
FIG. 4 is a perspective view of an alternate embodiment of the vial seal of the present invention.

In one alternate embodiment of the vial seal 10 of the present invention (FIG. 4), the first surface 13 can include an additional cross-contamination protective means such as a projecting ring surrounding each insert 14 which fits around the neck 32 of each reagent containment vial 30 when the inserts 14 of cover 12 engage the vials 30. This additional protective ring serves as a shield to minimize cross-contamination.

In this alternative embodiment of the vial seal 10 of the present invention (FIG. 4.), each insert 14 is at least partially surrounded by a flange (or protective ring) 40 spaced radially around each of the inserts 14. The purposes of flanges 40 is to prevent touch contamination of the inserts 14 when the user is either inserting or removing inserts 14 into vials 30. If the user touches a first insert 14 while opening or closing a vial 30, the reagent on that insert may rub off on the users fingers and contaminate another insert 14 when that is either being inserts or removed from a second vial. Thus, flanges 40 aid in preventing cross-contamination of the reagents from one vial 30 to the other. Furthermore, the user can contaminate the reagent vials 30 with foreign matter by touching an insert 14. Having radial flanges 40 or some other means to resist touch contamination of inserts 14 reduces the opportunities for cross- or touch-contamination.

In a second alternate embodiment of the vial seal 10 of the present invention (FIG. 5), in which the reagent pack 40 contains four vial spaces 54, but only three vials 30, two of the three vial inserts 14 are located at the left end 51 of the reagent pack 40 and the third vial insert 14 is positioned at the right end 52 of the reagent pack 40. No vial 30 is contained in the fourth vial space 53 of the reagent pack 40.

The first portion 11 and third portion 50 of the pliable cover 12 have formed thereon a series of vial inserts 14. Each of the vial inserts 14 corresponds to one of the three openings of the three vials 30 which are located in the reagent pack 40. Additionally, each of the vial inserts 14 is at least partially surrounded by a flange 55. The first portion 11 and third portion 50 of the pliable cover 12 may be of the wing-type configuration or of the non-wing-type configuration depicted in FIG. 5. They may be the same or different. Other configurations may also be used for convenience and to accommodate various reagent pack configurations. In this embodiment of the vial seal 10 of the present invention, the two vial inserts 14 which are located on the first portion 11 of the pliable cover 12 may be inserted into the two vial openings 30 positioned nearest to the first portion 11 of the pliable cover 12. The vial insert 14 which is located at the end of the first portion 11 of the pliable cover 12, and which is the top-most vial insert 14 depicted in FIG. 5, will be inserted into the opening of the vial 30 which is in the middle of the three vials 30 which are contained in the reagent pack 40. The other vial insert 14 which is contained on the first portion 11 of the pliable cover 12 will be inserted into the vial 30 which is located at the left end 51 of the reagent pack 40. The vial insert 14 which is located on the third portion 50 of the pliable cover 12 will be inserted into the opening of the vial 30 which is located at the right end 52 of the reagent pack 40. When the second portion 21 of the vial seal 10 is placed over the neck 32 of the three vials 30 in this manner, the ribs 33 formed in the pliable cover 12 allow the third portion 50 of the pliable cover 12 to be folded backwards and downwards into the empty fourth vial space 53 of the reagent pack 40 for convenient storage while it is desired to have the vial openings 30 remain in an uncovered state. This permits reactions to be performed without having the third portion 50 of the pliable cover 12 be in the way, so that the third portion 50 of the pliable cover 12 does not interfere with the operation of a clinical analyzer or other instrument.

The second portion 21 of the pliable cover 12 contains a series of openings 24, each of which corresponds to one of the vials 30 in the reagent pack 40. Each of the openings 24 preferably has a plurality of scores 22 extending radially therefrom and cut into the pliable cover 12.

Figure 5:
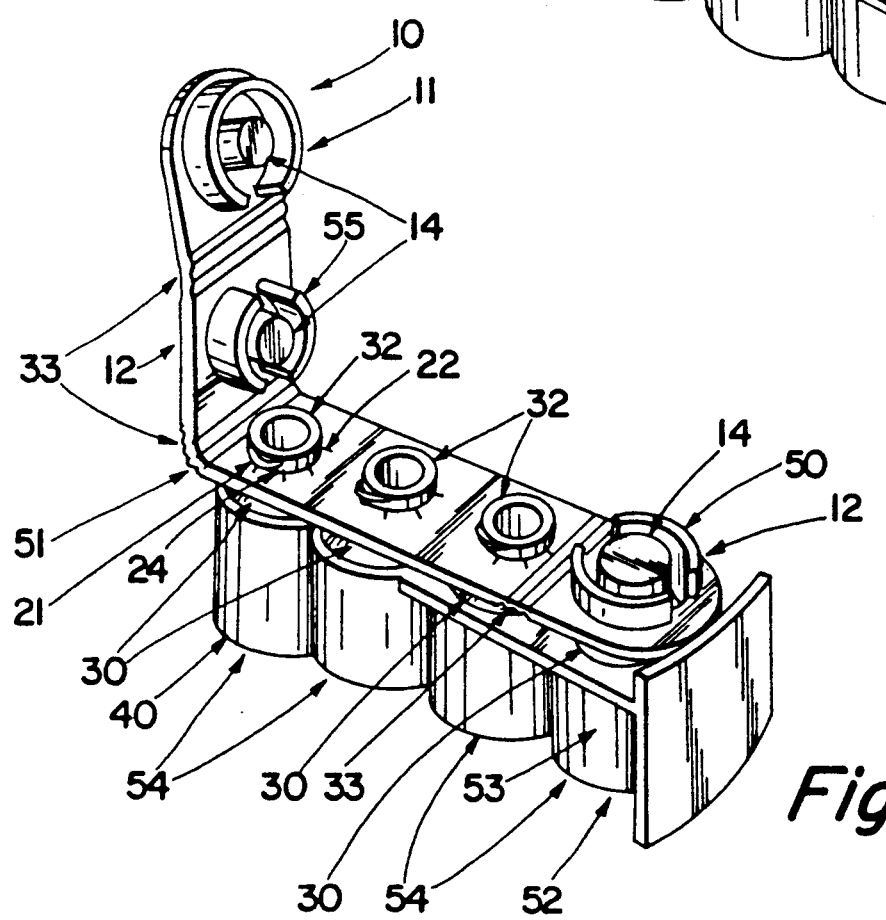
FIG. 5 is a perspective view of a second alternate embodiment of the vial seal of the present invention.

As is true with respect to all of the embodiments of the vial seal 10 of the present invention, this second alternate embodiment may contain fewer or more vial inserts 14 than are shown in FIG. 5, so that the vial seal 10 may be used with reagent packs 40 which contain fewer or more than three vials 30. With respect to the vial seal 10 illustrated in FIG. 5, any number of additional vial inserts 14 may be added to only the first portion 11 of the pliable cover 12, to only the third portion 50 of the pliable cover 12, or to both the first portion 11 and the third portion 50 of the pliable cover 12. Additionally, the second portion 21 of the pliable cover 12 may contain any number of openings 24, depending upon the number of vials 30 which will be contained in the reagent pack 40.

Alternatively, and preferably, the second portion 21 of the pliable cover 12 of the vial seal 10 may be placed on the reagent pack 40 in the opposite manner, such that the first portion 11 of the pliable cover 12 of the vial seal 10 will be located at the right end 52 of the reagent pack 40 and the third portion 50 of the pliable cover 12 will be located at the left end 51 of the reagent pack 40. When the second portion 21 of the vial seal 10 is placed over the neck 32 of the three vials 30 in this manner, the ribs 33 which are formed in the pliable cover 12 allow the first portion 11 of the pliable cover 12 to be folded backwards and downwards into the empty fourth vial space 53 of the reagent pack 40 for convenient storage while it is desired to have the vial openings 30 remain in an uncovered state so that reactions may be performed without interference of the first portion 11 of the pliable cover 12 with the operation of a clinical analyzer or other instrument.

Figure 6:
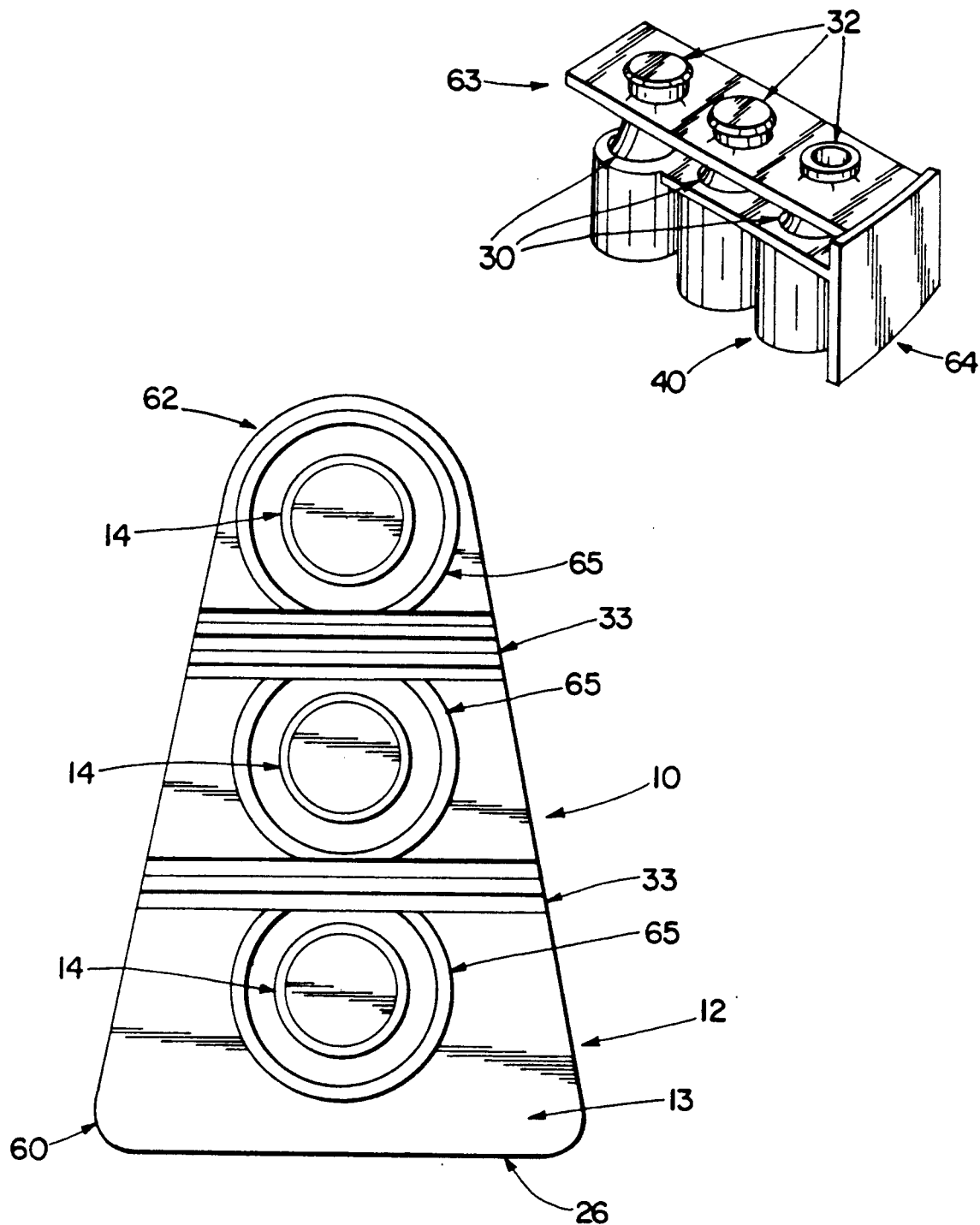
FIG. 6 is a perspective view of a third alternate embodiment of the vial seal of the present invention.

A third alternate embodiment (FIG. 6) of the vial seal 10 of the present invention consists of a pliable cover 12 which has a first 13 and a second 26 surface and which has formed on the first surface 13 a series of vial inserts 14, each of which corresponds to an opening of a vial 30 which is mounted in a reagent pack 40. In this embodiment of the present invention, the pliable cover 12 does not contain a corresponding plurality of openings which fit around the necks 32 of the vials 30. Although the vial seal 10 which is illustrated in FIG. 6 only has three vial inserts 14, any number of vial inserts 14 may be contained on the vial seal 10, depending upon the particular reagent pack 40 and upon the number of vials 30 which will be mounted in the reagent pack 40. The vial inserts 14 are formed along the first surface 13 of the pliable cover 12 at spacings corresponding to the spacings of the necks 32 of each of the vials 30. Each vial insert 14 is at least partially surrounded by a flange 65 spaced radially around each of the inserts 14. Either or both ends 60 and 62 of the vial seal 10 may be of a wing-type configuration or a non-wing-type configuration. They may be the same or different. Other configurations may also be used for convenience and to accommodate various reagent pack configurations. Either end 60 and 62 of the vial seal 10 may be placed at either end 63 and 64 of the reagent pack 40. Thus, in FIG. 6, the upper end 62 of the vial seal 10 could be positioned at either the left end 63 or the right end 64 of the reagent pack 40. The same is true with respect to the lower end 60 of the vial seal 10. Ribs or joints 33 are preferably formed in the pliable cover 12 intermediate to each of the vial inserts 14 to facilitate bending of the cover 12 and, further, to allow any of the vial inserts 14 to be inserted into the opening of a vial 30, while allowing any number of other vial inserts 14 not to be inserted into the opening of a vial 30.

While the invention has been described in connection with the presently preferred embodiments thereof, it will be apparent to those skilled in the art that various changes and modifications to the structure, arrangement, portions, elements, materials and components used in the practice of the invention are possible without departing from the scope and spirit of the invention. The foregoing description is therefore to be taken as illustrative rather than limiting and the scope of the invention is defined solely by the following claims and their equivalents.

What is claimed is:

1. A vial seal comprising:
   a unitary foldable member, having a mounting portion and a cover portion adapted to overlie said mounting portion;
   a plurality of vial insert means formed on said cover portion of said foldable member for sealing a plurality of vials; and a corresponding plurality of openings formed in said mounting portion of said foldable member for supporting the plurality of vials whereby said foldable member permits sealing and unsealing of the vials by said inserts; said openings including a plurality of score means extending into said mounting portion for facilitating the attachment and retention of the vials.

* * * * *